(12) United States Patent
Mythen

(10) Patent No.: US 7,592,018 B2
(45) Date of Patent: Sep. 22, 2009

(54) TONGUE CLEANING APPARATUS

(76) Inventor: Daniel Richard Mythen, 21307 NE. 97th Pl., Redmond, WA (US) 98053

(*) Notice: Subject to any disclaimer, the term of this patent is extended or adjusted under 35 U.S.C. 154(b) by 0 days.

(21) Appl. No.: 11/093,785

(22) Filed: Mar. 29, 2005

(65) Prior Publication Data

US 2006/0222683 A1   Oct. 5, 2006

(51) Int. Cl.
*A61K 9/68* (2006.01)
(52) U.S. Cl. ...................................... 424/440
(58) Field of Classification Search ............ 15/111, 15/210, 104.93
See application file for complete search history.

(56) References Cited

U.S. PATENT DOCUMENTS

| 4,079,478 | A | * | 3/1978 | Andrews, Sr. | 15/210.1 |
| 4,432,114 | A | * | 2/1984 | Goudsmit | 15/104.93 |
| 5,226,197 | A | * | 7/1993 | Nack et al. | 15/111 |
| 6,004,334 | A | * | 12/1999 | Mythen | 606/161 |
| 2006/0193909 | A1 | * | 8/2006 | Stawski et al. | 424/464 |

* cited by examiner

*Primary Examiner*—Carlos A. Azpuru
(74) *Attorney, Agent, or Firm*—Vierra Magen Marcus & DeNiro LLP

(57) ABSTRACT

The present invention is a dissolvable candy which provides effective tongue scraping action. The candy is a soft pliable edible dissolvable candy material, such as a GUMMI-BEAR type confection, having a generally oval shape. A plurality of segments are formed with hard candy in one surface of the soft candy. Preferably, the segments have raised ridges which are suitable for abrading the tongue. A blister have a freshening agent is formed on the same side as the hard candy segments. A plurality of depressions are formed in another side of the soft candy to facilitate adhering the soft candy to the roof of the mouth.

12 Claims, 1 Drawing Sheet

TONGUE CLEANING APPARATUS

FIELD OF THE INVENTION

The present invention relates to a tongue cleaning apparatus, and more specifically to an oval-shaped candy which is soft and pliable for removably adhering to the roof of the user's mouth, and having hard candy segments formed in the surface of the soft candy for gently abrading the tongue to remove malodorous films.

BACKGROUND OF THE INVENTION

Oral malodor, also known as bad breath or halitosis, is a common condition afflicting many people. The origin of oral malodor may be physiological or pathological in nature. However, even for individuals having healthy periodontal tissues and practicing good oral hygiene, the back of the tongue is a significant source of oral malodor due to the production of volatile sulfur compounds.

Various devices are known for addressing oral malodor. For example, U.S. Pat. No. 5,226,197 discloses a tongue hygiene device shaped like a toothbrush but with a wider than normal head, short bristles and a scraper. Applicant's prior U.S. Pat. No. 6,004,334 discloses a candy having a soft side and a hard side, wherein the hard side has a raised pattern to help scrape the tongue. However, it remains desirable to find have an easy-to-use device that helps fight oral malodor, and the present invention is directed to such a device.

SUMMARY OF THE INVENTION

The present invention is a dissolvable candy which provides effective tongue scraping action. The candy is a soft pliable edible dissolvable candy material, such as a GUMMI-BEAR type confection, having a generally oval shape. A plurality of hard candy segments are formed in one surface of the soft candy. Preferably, the segments have raised ridges which are suitable for abrading the tongue. Also, a plurality of depressions are formed in another side of the soft candy to facilitate adhering the soft candy to the roof of the mouth.

In use, the soft candy is adhered to the roof of the mouth and the user's tongue passes over the hard candy segments formed in the soft candy. Preferably, the soft candy is repeatedly removed and adhered in a new spot to permit more thorough coverage of the tongue until the candy is dissolved.

A better understanding of the features and advantages of the present invention will be obtained by reference to the following detailed description of the invention and accompanying drawings which set forth an illustrative embodiment in which the principles of the invention are utilized.

DETAILED DESCRIPTION OF THE INVENTION

Figure 1:
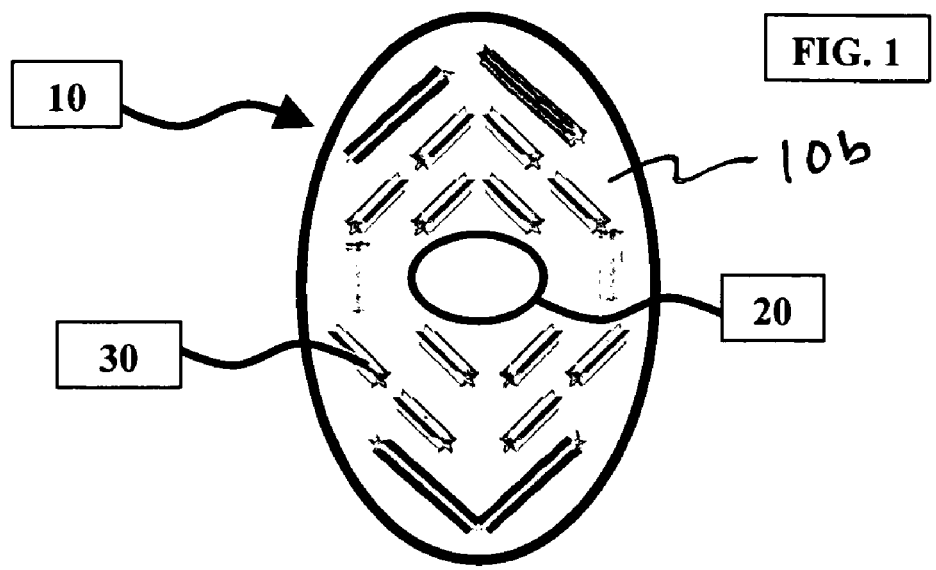
FIG. 1 is a bottom plan view of the preferred embodiment of a tongue cleaning apparatus in accord with the present invention.
Figure 2:
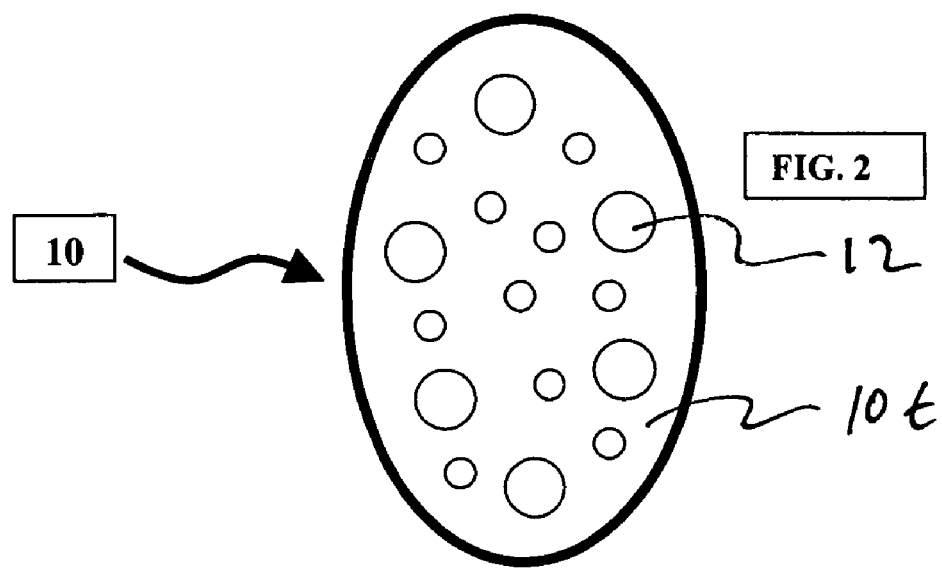
FIG. 2 is a top plan view of the tongue cleaning apparatus of FIG. 1.
Figure 3:
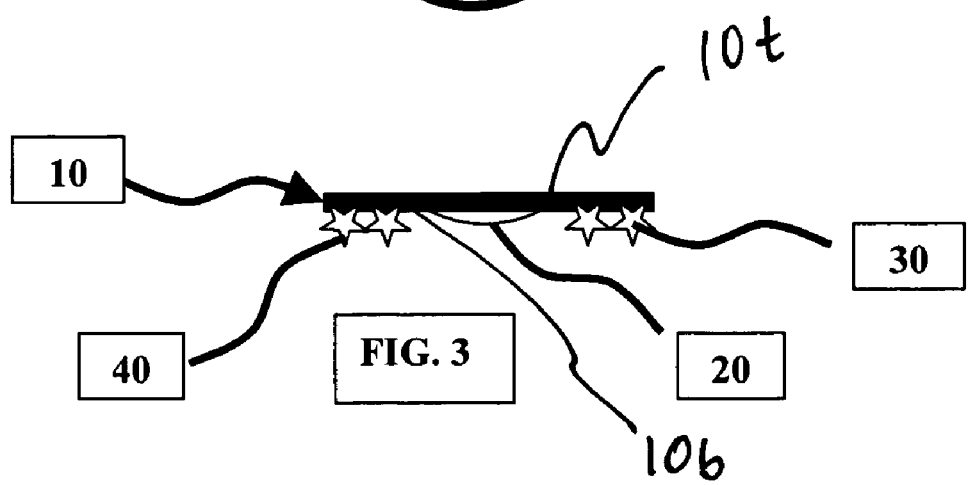
FIG. 3 is a side plan view of the tongue cleaning apparatus of FIG. 1.

Referring to FIGS. 1-3, the present invention includes a generally oval-shaped candy 10 made of soft edible material. In the preferred embodiment, the width of the candy 10 is approximately ¾ inch to 1 inch. The length of the candy is approximately 1 inch to 1¾ inch, and the thickness of the candy is approximately ⅛th inch to ⅜ inch.

The main body 10 is preferably a soft, pliable, dissolvable gelatinous or gum candy material, such as that used in GUMMI-BEAR or GUMMI-WORM type confections. A circular or oval blister 20 is formed on the bottom 10b of the candy using conventional confectionary techniques. The blister 20 is filled with a liquid freshening and/or disinfecting agent (not shown), for example, mouthwash, which is released onto the top of the tongue during use.

The top side 10t of candy 10 is generally smooth, but is formed to have small circular depressions 12 (resembling suction cups) that measure ⅛ inch to ⅜ inch in diameter and 1/64 inch to 1/32 inch deep. These depressions 12 are intended to assist the candy in adhering firmly to the roof and soft palate of the mouth while the tongue moves across the scraping surface. The suction cups may be in a random or geometric pattern across the top face of the candy.

The bottom side 10b of candy 10 is imbedded with multiple hard candy segments 30 approximately ⅛ inch to ⅜ inch long and approximately ⅛ inches wide with raised scraping ridges 40 forming a scraping surface that abrades the tongue as it passes under the candy. The hard candy segments 30 are preferably formed with a hard dissolvable candy material, such as any commercially available hard peppermint candy. The hard candy material is formed by conventional confectionery methods to have a pattern, such as by extruding, molding or stamping. For example, the illustrated pattern 30 is a five-point star defined by ridges 40 which extend from the surface of the soft candy body approximately 1/16 inch high. The ridges 40 provide a rigid scraping surface that abrades the tongue as it passes under the candy. Other patterns with more ridges may prove equally effective.

In use, the candy 10 may be repeatedly removed and reapplied to different positions in the mouth. By moving the position of the candy in the mouth, a more thorough coverage of the tongue by the abrasive scraping action of the candy is provided. Such action may be repeated until the candy is fully dissolved.

It should be understood that the invention is not intended to be limited by the specifics of the above-described embodiment, but rather defined by the accompanying claims. For example, dimensions and materials are specified for the preferred embodiment, but many variations will be obvious to one with skill in such matters.

I claim:

1. A tongue cleaning apparatus, comprising a soft, pliable, dissolvable candy having a generally oval shape, wherein a plurality of hard candy segments are formed on a first surface of the soft candy.

2. A tongue cleaning apparatus as in claim 1, wherein the hard candy segments are embedded into the first surface of the soft candy.

3. A tongue cleaning apparatus as in claim 1, wherein the hard candy segments include raised ridges.

4. A tongue cleaning apparatus as in claim 2, wherein the hard candy segments include raised ridges.

5. A tongue cleaning apparatus as in claim 1, further comprising a plurality of depressions formed on a second surface of the soft candy.

6. A tongue cleaning apparatus as in claim 1, further comprising a blister formed in the first surface of the soft candy.

7. A tongue cleaning apparatus, comprising a soft, pliable, dissolvable candy having a generally oval shape, wherein a plurality of hard candy segments are formed on a surface of the soft candy, wherein a plurality of depressions are formed on another surface of the soft candy.

8. A tongue cleaning apparatus as in claim 6, wherein the blister contains a freshening agent.

9. A tongue cleaning apparatus as in claim 6, wherein the blister contains a disinfecting agent.

10. A tongue cleaning apparatus as in claim 7, further comprising a blister formed in the surface of the soft candy.

11. A tongue cleaning apparatus as in claim 10, wherein the blister contains a freshening agent.

12. A tongue cleaning apparatus as in claim 10, wherein the blister contains a disinfecting agent.

\* \* \* \* \*